United States Patent
Nakao et al.

[11] Patent Number: 5,374,273
[45] Date of Patent: Dec. 20, 1994

[54] MEDTHOD FOR RETRIEVAL OF RETAINED COMMON BILE DUCT STONES

[76] Inventors: Naomi L. Nakao, 303 E. 57th St., New York, N.Y. 10022; Peter J. Wilk, 185 W. End Ave., New York, N.Y. 10023

[21] Appl. No.: 957,416
[22] Filed: Oct. 5, 1992
[51] Int. Cl.$^5$ .............................................. A61B 17/22
[52] U.S. Cl. .................... 606/127; 128/898
[58] Field of Search ................ 606/113, 114, 127, 47, 606/41; 128/898; 43/7, 11

[56] References Cited

U.S. PATENT DOCUMENTS

| | | | |
|---|---|---|---|
| 404,946 | 6/1889 | Andersson | 43/11 |
| 1,585,483 | 5/1926 | Freer | 43/7 |
| 3,715,829 | 2/1973 | Hamilton | |
| 4,202,338 | 5/1980 | Bitrolf | |
| 4,326,530 | 4/1982 | Fleury, Jr. | |
| 4,345,599 | 8/1982 | McCarrell | |
| 4,493,320 | 1/1985 | Treat | |
| 4,503,855 | 3/1985 | Maslanka | |
| 4,516,347 | 5/1985 | Dickie | |
| 4,557,255 | 12/1985 | Goodman | |
| 4,638,802 | 1/1987 | Okada | |
| 4,643,187 | 2/1987 | Okada | |
| 4,705,041 | 11/1987 | Kim | 606/108 |
| 4,718,419 | 1/1988 | Okada | |
| 4,800,870 | 1/1989 | Reid, Jr. | |
| 4,997,435 | 3/1991 | Demeter | 606/127 |
| 5,084,054 | 1/1992 | Bencini et al. | 606/113 |
| 5,195,954 | 3/1993 | Schnepp-Pesch et al. | 606/127 |

FOREIGN PATENT DOCUMENTS

| | | | |
|---|---|---|---|
| 2938259 | 4/1981 | Germany | 606/47 |
| 3347122 | 6/1985 | Germany | 606/47 |

*Primary Examiner*—Tamara L. Graysay
*Attorney, Agent, or Firm*—R. Neil Sudol; Henry D. Coleman

[57] ABSTRACT

A method for the removal of retained common bile duct stones includes the steps of introducing a distal end of a flexible tubular member into the common bile duct and ejecting from the distal end of the tubular member a loop to which a flexible web is attached to form a capture pocket. The loop and the pocket are expanded from a collapsed configuration upon ejection of the loop from the distal end of the tubular member. The loop and the pocket are moved through the common bile duct to capture a retained stone in the pocket. Subsequently, the loop and the pocket are at least partially closed by drawing the loop and the pocket in a proximal direction into the distal end of the tubular member, thereby enclosing the captured stone in the pocket. The tubular member and the contracted loop and pocket are withdrawn from the common bile duct, thereby removing the captured stone from the common bile duct. The loop may be bent to form a right angle in an unstressed opened configuration, while the capture pocket may be formed with a trap door or flap for preventing the loss of stones once they are caught in the capture pocket.

12 Claims, 3 Drawing Sheets

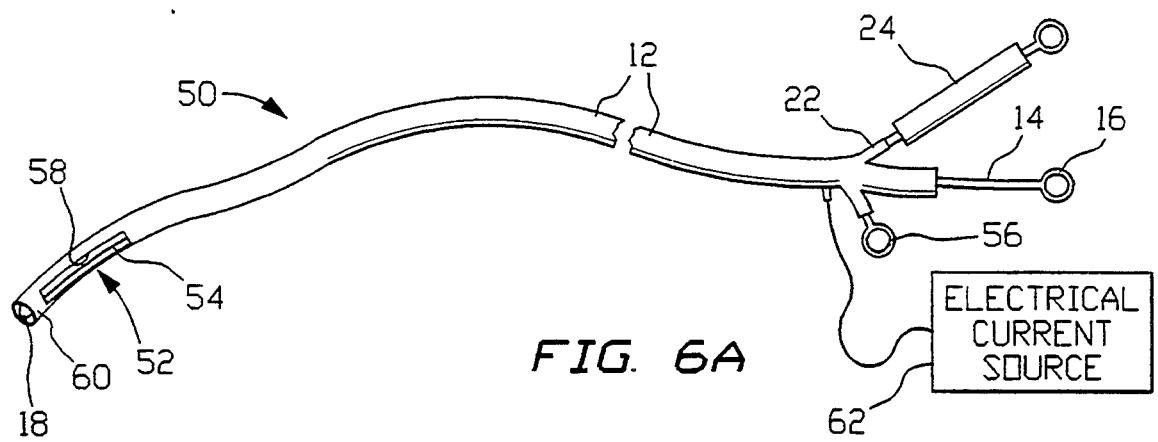
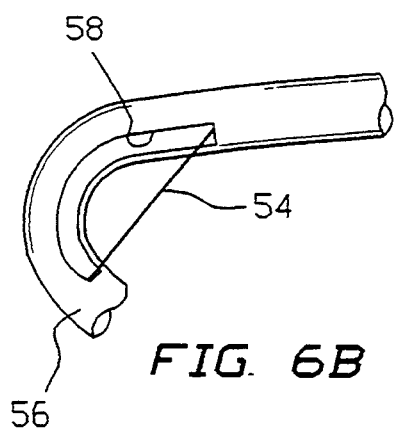
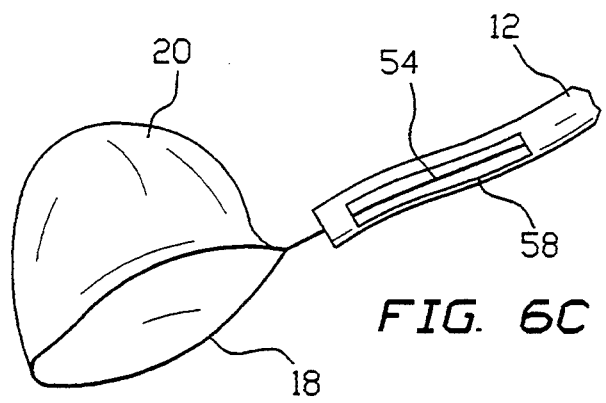
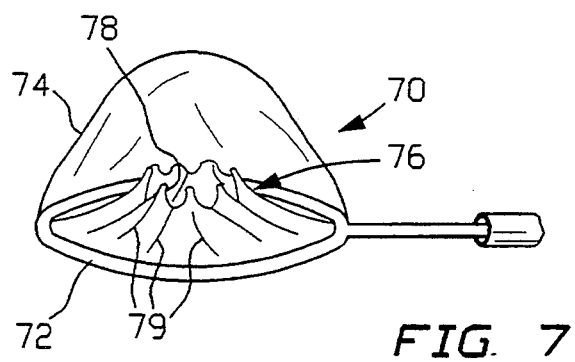
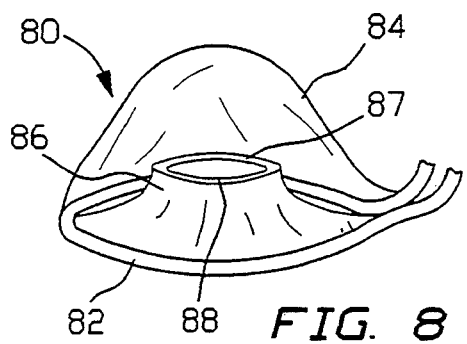

MEDTHOD FOR RETRIEVAL OF RETAINED COMMON BILE DUCT STONES

BACKGROUND OF THE INVENTION

This invention relates to a method for the surgical retrieval of retained common bile duct stones. This invention also relates to an instrument assembly utilizable in performing the method.

A common affliction, particularly among older people, is gall stones, i.e., small stones formed from natural biological processes from chemical substances in the bile. These stones sit in the gall bladder and are frequently removed during a cholecystectomy. In a cholecystectomy, the cystic duct is clamped and severed and the gall bladder is removed, thereby removing any stones in the bladder. However, some stones are frequently retained in the common bile duct.

Currently, the stones in the common bile duct are retrieved using a DORMIA type retrieval basket. That instrument includes a series of wires of spring biased construction which are connected to form an ovoidal or football shaped cage upon the release of the basket from the distal end of a tubular member.

The distal end of the tubular member is inserted through the Ampulla of Vater at one end of the common bile duct or, alternatively, through a bile duct over the liver. The DORMIA type retrieval basket may also be inserted through a tubular prosthesis or bridge extending from the abdominal wall to the wall of the common bile duct where the bridging member is inserted into the duct.

A DORMIA type retrieval basket is difficult to manipulate in order to capture retained common bile duct stones. Such operations can take hours for an essentially simple task. The task is made even more difficult and time consuming if several stones are to be retrieved from the duct.

OBJECTS OF THE INVENTION

An object of the present invention is to provide an improved technique for retrieving retained common bile duct stones.

Another object of the present invention is to provide such a method which is relatively easy to use.

A further object of the present invention is to provide an instrument assembly for use in retrieving retained common bile duct stones.

Yet another object of the present invention is to provide such an instrument assembly which is adapted for the removal of several stones in the same operation, without the necessity for removing and reinserting the instrument assembly to subsequently capture other stones.

These and other objects of the present invention with be apparent from the drawings and detailed descriptions herein.

SUMMARY OF THE INVENTION

A method for the removal of retained common bile duct stones comprises, in accordance with the present invention, the steps of (a) introducing a distal end of a flexible tubular member into the common bile duct, (b) ejecting from the distal end a loop to which a flexible web is attached to form a capture pocket, (c) expanding the loop and the pocket from a collapsed configuration upon ejection of the loop from the distal end, (d) moving the loop and the pocket through the common bile duct to capture a retained stone in the pocket, (e) at least partially closing the loop and the pocket by drawing the loop and the pocket in a proximal direction into the distal end of the tubular member, thereby enclosing the captured stone in the pocket, and (f) withdrawing the tubular member and the contracted loop and pocket from the common bile duct, thereby removing the captured stone from the common bile duct.

According to another feature of the present invention, the introduction of the distal end of the tubular member into the common bile duct is implemented by (i) inserting an endoscope through the stomach and into the upper intestinal tract, (ii) ejecting the tubular member from a biopsy channel in the endoscope, and (iii) inserting the distal end of the tubular member through the Ampulla of Vater into the common bile duct. In that event, the tubular member may be provided with a longitudinally extending elongate window at the distal end and a cauterization wire fastened to the distal end. The method then additionally comprises the steps of (g) exerting tension on the wire upon an ejection of the tubular member from the biopsy channel, thereby bending the tubular member at the distal end to expose a section of the wire through the window, (h) manipulating the tubular member to bring the exposed section of the wire into contact with the Ampulla of Vater, and (i) energizing the wire to cauterize organic tissues during the step of manipulating, thereby enlarging an opening into the common bile duct.

According to another feature of the present invention, the method also comprises the steps of injecting a radio-opaque fluid into the common bile duct through the tubular member upon insertion of the distal end into the common bile duct, and using an X-ray machine to visually inspect the common bile duct for the locations of stones therein prior to and during the step of moving.

In accordance with a specific embodiment of the present invention, where an endoscope is passed through the stomach and into the upper intestinal tract, the method includes the steps of ejecting a daughter scope from the biopsy channel, inserting a distal end of the daughter scope through the Ampulla of Vater into the common bile duct, and using the daughter scope to inspect the common bile duct for retained stones, the tubular member being ejected from the daughter scope into the common bile duct.

According to an alternative feature of the present invention, the introduction of the distal end of the tubular member into the common bile duct is implemented by connecting a tubular prosthesis to the common bile duct so that the tubular prosthesis communicates with the common bile duct, and inserting the distal end of the tubular member through the tubular prosthesis and into the common bile duct. The tubular prosthesis may include a tubular T-bar at an inner end. In that case, the connection of the tubular prosthesis to the common bile duct is accomplished in part by disposing the T-bar inside the common bile duct.

According to a further feature of the present invention, the loop is expanded or opened to a configuration having a bend so that the expanded loop lies in two planes oriented at an angle with respect to one another. In that case, the expanded loop is pushed in a direction away from the distal end of the tubular member and towards the retained common bile duct stone.

According to an alternative feature of the present invention, the introduction of the distal end of the tubular member into the common bile duct is implemented by inserting the distal end of the tubular member through a patient's skin directly into a bile duct over the liver and from thence into the common bile duct.

According to yet another feature of the present invention, the pocket is formed with a trap door and the method further comprises the steps of closing the trap door upon capture of the stone in the pocket and moving the loop to capture another retained common bile duct stone in the pocket.

A surgical instrument assembly for use in the retrieval of retained common bile duct stones comprises, in accordance with a particular embodiment of the present invention, an elongate flexible tubular member and an elongate rod member having a limited degree of flexibility. The rod member is slidably inserted through the tubular member and is longer than the tubular member. A flexible loop is connected to the rod member at a distal end thereof and has a spring bias construction tending to form the loop into an opened configuration having a bend so that a portion of the opened loop, upon an ejection from the tubular member, defines a plane oriented substantially orthogonally with respect to the tubular member at the distal end thereof. The loop is disposed in a straightened and collapsed configuration at least partially inside the tubular member distally of the distal end of the rod member. A flexible web member is connected to the loop to form a capture pocket, the loop defining a mouth opening of the pocket.

Pursuant to another feature of the present invention, the loop in the opened configuration lies essentially in two planes oriented at an angle, preferably a right angle, with respect to one another.

Pursuant to a further feature of the present invention the tubular member is provided with a longitudinally extending elongate window at a distal end and a cauterization wire fastened to such distal end of the tubular member. An actuator is connected to the wire at a proximal end thereof for enabling a user to exert tension on the wire to expose a section of the wire through the window. An electrical power source is operatively connected to the wire for electrically energizing the wire to cauterize organic tissues upon exposure of the wire section through the window in the tubular member.

Pursuant to yet another feature of the present invention, the tubular member is provided at a proximal end with means for connecting the tubular member to a pressurizable source of radio-opaque fluid.

In addition, the capture pocket is formed with a trap door or valve flap proximate to the mouth opening.

An instrument assembly provided with a capture pocket having a trap door in accordance with the present invention is adapted for the removal of several stones in the same operation, without the necessity for removing and reinserting the instrument assembly to subsequently capture other stones.

An instrument assembly provided with an integral injection port for radio-opaque fluid in accordance with the present invention simplifies retrieval of common bile duct stones insofar as it is not necessary to insert a separate instrument for injecting the fluid. The fluid injection and the stone capture are accomplished by the same instrument assembly. In addition, the same instrument assembly may be used to open the Papilla of Vater.

An instrument assembly in accordance with the present invention facilitates the retrieval of common bile duct stones also because a loop with a capture pocket, particularly a loop with a 90° bend, is easier to use than a conventional DORMIA type retrieval basket.

BRIEF DESCRIPTION OF THE DRAWING

FIG. 6A is a schematic perspective view of another modified snare device in accordance with the present invention.

FIG. 6B is a partial perspective view of the modified snare device of FIG. 6A, depicting an operational configuration of that device.

FIG. 6C is a partial perspective view of the modified snare device of FIG. 6A, depicting another operational configuration of that device.

FIG. 7 is a schematic perspective view of yet another modified snare device in accordance with the present invention.

FIG. 8 is a schematic perspective view of an additional modified snare device in accordance with the present invention.

The same elements and organs in the different figures bear the same reference designations.

DETAILED DESCRIPTION

Figure 1:
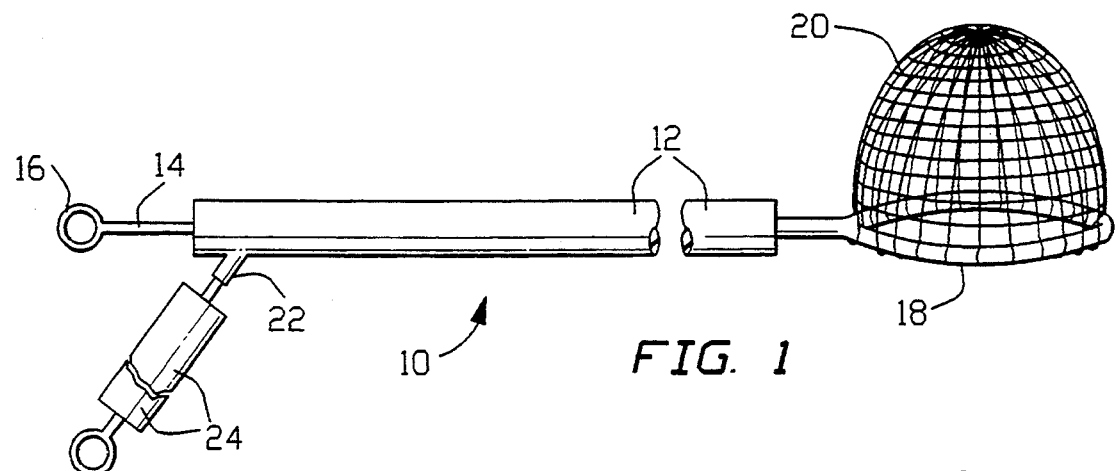
FIG. 1 is a schematic side elevational view of a snare device for use in retrieving retained common bile duct stones, in accordance with the present invention.

As illustrated in FIG. 1, a surgical instrument assembly 10 for use in the retrieval of retained common bile duct stones comprises an elongate flexible tubular member 12 and an elongate rod or wire member 14 having a limited degree of flexibility, the rod being slidably inserted through the tubular member. Rod 14 is longer than tubular member 12 and is provided at a proximal end with a hand or finger grip 16 and at a distal end with a flexible loop 18 having a spring bias construction tending to form the loop into an opened configuration, as depicted in FIG. 1. Loop 18 is disposed in a collapse configuration at least partially inside tubular member 12 distally of the distal end of rod 14 prior to a stone retrieval operation. A flexible web member 20 is connected to loop 18 to form a capture pocket. Loop 18 defines a mouth opening of the capture pocket. A port 22 is provided at a proximal end of tubular member 12 for connecting the tubular member to a pressurizable source of radio-opaque fluid such as a syringe 24.

Figure 2:
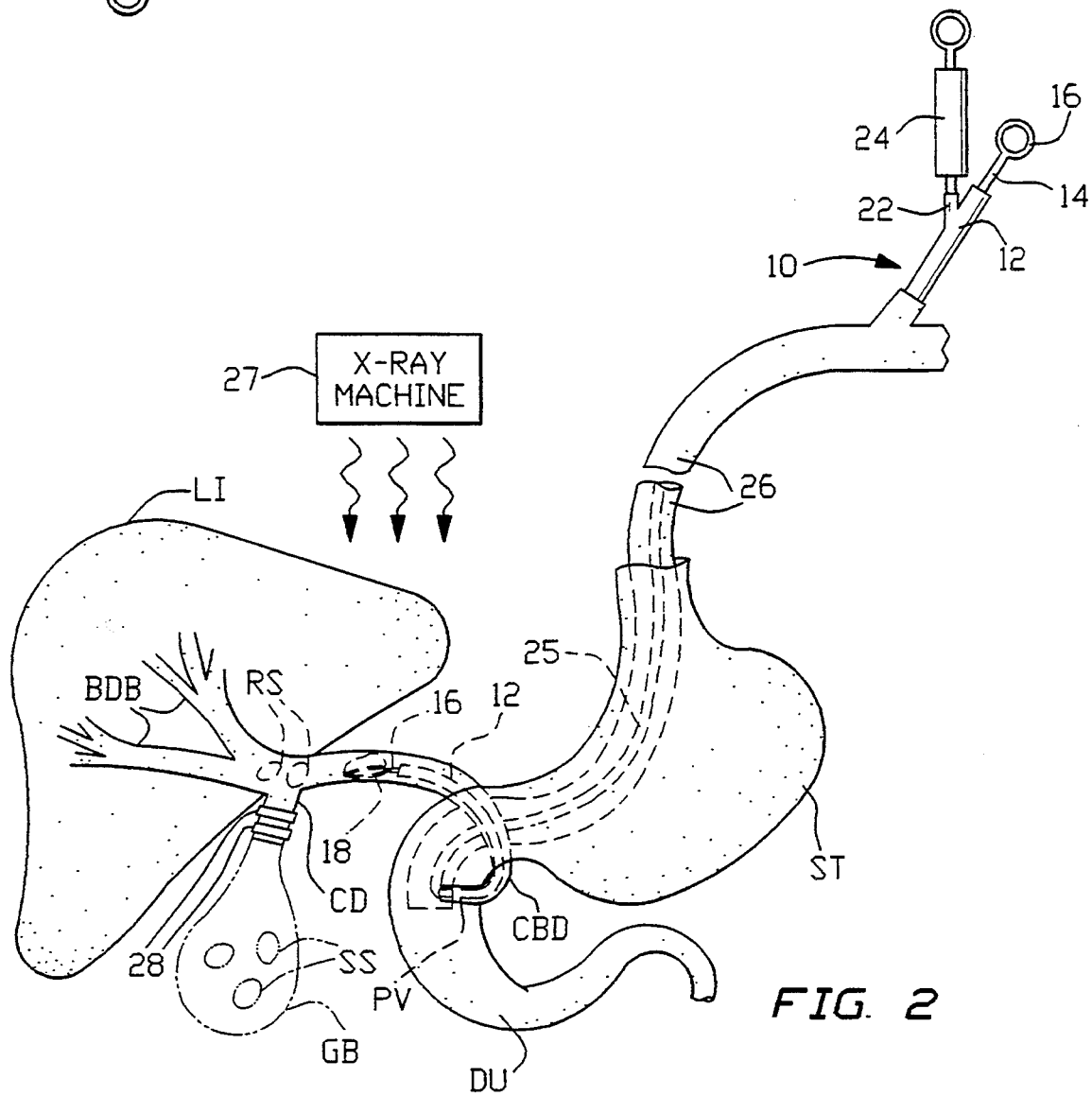
FIG. 2 is a schematic elevational view of portions of the digestive tract, showing use of the snare device of FIG. 1 in conjunction with an endoscope.

In order to be used in conjunction with an endoscope 26, as illustrated in FIG. 2, tubular member 12 is sufficiently narrow to fit down the biopsy channel 25 of the endoscope. Endoscope 26 is inserted through the mouth (not shown) of a patient and through the stomach ST into the duodenum DU. Upon visually detecting, via endoscope 26, the Papilla of Vater PV at the lower end of the common bile duct CBD, a surgeon pushes tubular member 12 in a distal direction through the biopsy channel so that the tubular member emerges from the distal end of the biopsy channel and enters common bile duct CBD through the Papilla of Vater PV.

Upon a sufficient insertion of tubular member 12 into common bile duct CBD, source 24 of radio-opaque fluid is pressurized to dispense the fluid out the distal end of tubular member 12 into the common bile duct. X-ray equipment 27 is then used in a conventional procedure to locate retained stones RS in the common bile duct CBD. Subsequently, hand or finger grip 16 is manipulated to push rod 14 in a distal direction through tubular member 12 to eject loop 18 and web or pocket 20 from the tubular member and into the common bile duct CBD. Upon ejection, loop 18 and pocket 20 automatically expand, under the spring biased action of the loop, from a collapsed storage configuration to an opened use configuration. Finger grip 16 and tubular member 12 are then manipulated to capture the retained common bile duct stones RS. Upon capture of the stones RS, hand or finger grip 16 is pulled in the proximal direction to at least partially retract loop 18 and pocket 20 into the distal end of tubular member 12, thereby at least partially contracting the loop and the pocket to entrain and hold the retrieved stones RS. Subsequently, tubular member 12 is pulled in the distal direction relative to endoscope 26 to remove the tubular member from the common bile duct CBD and out through the Papilla of Vater PV. The entire assembly, including endoscope 26, is then extracted from the patient.

FIG. 2 also shows, in dot-dash lines, a gall bladder GB and stones SS which have been removed in a cholecystectomy. Two staples or clips 28 have been attached to the cystic duct CD to close that duct. The liver LI is connected to the common bile duct CBD via bile duct branches BDB.

Figure 3:
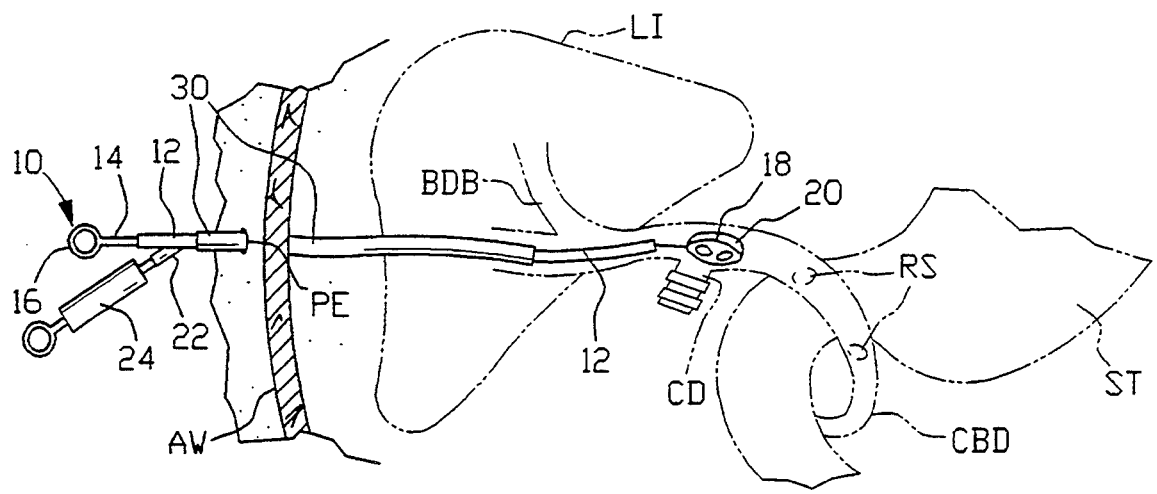
FIG. 3 is a schematic elevational view of portions of the digestive tract, showing another use of the snare device of FIG. 1.

FIG. 3 illustrates an alternative procedure using the snare device 10 of FIG. 1 to retrieve retained stones RS in common bile duct CBD subsequently to a cholecystectomy. A tubular port member 30 is disposed in the abdominal wall AW to traverse the wall. Tubular member 12 is dimensioned to be inserted through port member 30, as illustrated in FIG. 3. Port member 12 is inserted through abdominal wall AW and through a portion of liver LI into a selected bile duct branch BDB. To implement this procedure, a needle (not shown) is inserted inside the port member to pierce the abdominal wall AW, the liver LI and the selected bile duct branch BDB. An expander or other device is used in a conventional technique to expand the path through the liver LI prior to the insertion of tubular member 12. Upon disposition of port member 30 as illustrated in FIG. 3, the needle is removed and replaced with snare device 10.

The remainder of the procedure is essentially the same as the method described hereinabove with reference to FIG. 2. Upon a sufficient insertion of tubular member 12 into common bile duct CBD, source 24 of radio-opaque fluid is pressurized to dispense the fluid out the distal end of tubular member 12 into the common bile duct. X-ray equipment (not illustrated) is then used in a conventional procedure to locate retained stones RS in the common bile duct CBD. Subsequently, hand or finger grip 16 is manipulated to push rod 14 in a distal direction through tubular member 12 to eject loop 18 and web or pocket 20 from the tubular member and into the common bile duct CBD. Upon ejection loop 18 and pocket 20 automatically expand, under the spring biased action of the loop, from a collapsed storage configuration to an opened use configuration. Finger grip 16 and tubular member 12 are then manipulated to capture the retained common bile duct stones RS. Upon capture of the stones RS, hand or finger grip 16 is pulled in the proximal direction to at least partially retract loop 18 and pocket 20 into the distal end of tubular member 12, thereby at least partially contracting the loop and the pocket to entrain and hold the retrieved stones RS. Subsequently, tubular member 12 is pulled in the distal direction relative to port member 30 to remove the tubular member from the common bile duct CBD and the slected bile duct branch BDB. The entire assembly, including port member 30, is then removed though wall AW.

Figure 4A:
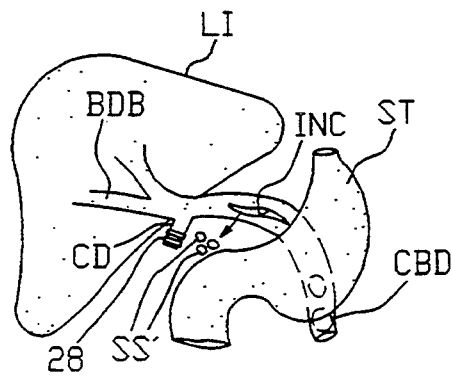
FIG. 4A is a schematic elevational view of portions of the digestive tract, showing an incision in the common bile duct made after a cholecystectomy.
Figure 4B:
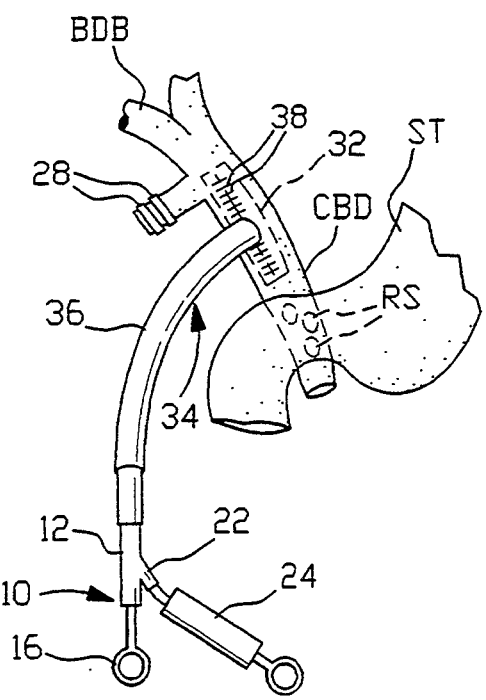
FIG. 4B is a schematic elevational view of portions of the digestive tract shown in FIG. 4A, illustrating a T-tube surgically inserted into the common bile duct and the snare of FIG. 1 inserted into the common bile duct via the T-tube.

FIGS. 4A and 4B depict another alternative procedure for retrieving retained stones RS in the common bile duct CBD. Upon completion of a cholecystectomy, wherein staples or clips 28 are clamped to the severed cystic duct CD, an incision INC is made in the common bile duct CBD. Any stones SS' visible in the duct are removed. A hollow cross-bar 32 of a tubular prosthesis or T-tube 34 with an elongate hollow shaft 36 is then inserted into the common bile duct CBD through incision INC. Upon that disposition of crossbar 32, incision INC is closed by sutures 38 (FIG. 4B). Shaft 36 is brought out through a perforation PE in the abdominal wall.

T-tube 34 is conventionally used to drain bile from the common bile duct CBD.

Upon the completed disposition of T-tube 34, snare device 10 is inserted through the T-tube and into the common bile duct CBD. Snare device 10 is then used as described hereinabove with reference to FIGS. 2 and 3 to remove retained common bile duct stones RS.

Figure 5:
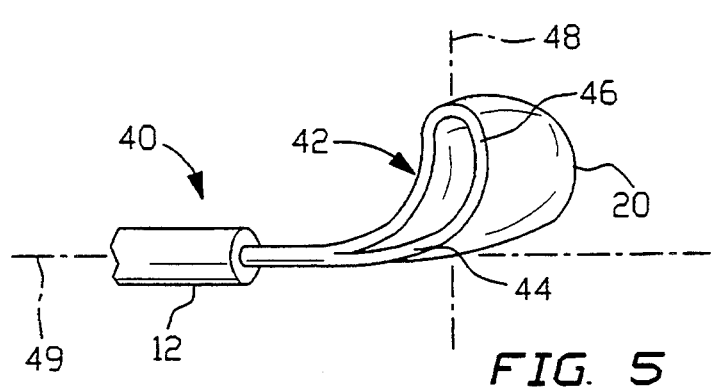
FIG. 5 is a partial side elevational view of a modified snare device in accordance with the present invention.

As illustrated in FIG. 5, another snare device or instrument assembly 40 for use in retrieving retained common bile duct stones includes the same elements as described above with reference to FIG. 1 except that a flexible loop 42 has a spring bias construction tending to form the loop into an opened configuration having a bend 44 so that a portion 46 of the opened loop, upon an ejection from tubular member 12, defines a plane 48 oriented substantially orthogonally with respect to a plane 49 of the tubular member at the distal end thereof. More particularly, loop 42 in the opened configuration lies essentially in two planes oriented at an angle, preferably a right angle, with respect to one another. Prior to ejection during a stone retrieval procedure, loop 42 is disposed in a straightened and collapsed configuration at least partially inside tubular member 12. Web or pocket 20 is connected to loop 42 so that the loop defines a mouth opening of the pocket.

The loop of FIG. 5 is specifically adapted for use in retrieving retained common bile duct stones. The angled configuration of the loop 42 facilitates collection of stones within the narrow confines of the common bile duct. Loop 42 need only be moved in an axial or longitudinal direction through the common bile duct. Generally, loop 42 with its capture pocket 20 is moved away from the distal end of tubular member 12 towards retained stones.

As illustrated in FIG. 6A, a further snare device or instrument assembly 50 for use in retrieving retained common bile duct stones includes the same elements as described above with reference to FIG. 1 except that tubular member 12 of snare device 50 is additionally provided with cauterization componentry 52 for use in enlarging the opening of the common bile duct at the Papilla of Vater. Cauterization componentry 52 includes a cauterization wire 54 extending longitudinally through tubular member 12 from an actuator handle 56 at a proximal end of the instrument, past an elongate window 58 to the distal tip 60 of tubular member 12. At distal tip 60, cauterization wire 54 is attached to tubular member 12. Accordingly, upon a pulling of wire 54 in a proximal direction via handle 56, a distal end portion of tubular member 12 which is roughly coextensive longitudinally with window 58 bends, as illustrated in FIG. 6B. Wire 54 emerges from tubular member 12 through window 58 and is energized with electrical current from a source 62 operatively connected to the wire.

Snare device 50 is used in conjunction with an endoscope, as described above with reference to FIG. 2. Upon ejection of a distal portion of tubular member 12 from the biopsy channel of the endoscope 26, handle 56 is pulled in the proximal direction, whereby wire 54 emerges through window 58, as shown in FIG. 6B. The distal end of tubular member 12 is then inserted though the Papilla of Vater. Current from source 62 cuts and cauterizes the tissues of the Papilla of Vater to enlarge the opening from the common bile duct CBD into the duodenum DU (FIG. 2). Upon completion of the enlarging procedure, handle 56 is pushed in the distal direction to straighten out the distal end portion of tubular member 12 and to retract wire 54 back into the tubular member through window 58. Tubular member 12 is then pushed into the common bile duct and hand or finger grip 16 manipulated to eject loop 18 and pocket 20, as illustrated in FIG. 6C. The procedure described hereinabove with reference to FIGS. 2 and 3 is then undertaken to retrieve retained stones.

As depicted in FIG. 7, another snare device or instrument assembly 70 includes a spring-biased loop 72 provided with a flexible capture pocket 74. An ancillary web 76 is attached to loop 72 and/or pocket 74 for forming a trap door. Retained common bile duct stones easily pass through an aperture 78 in web 76 to become lodged in capture pocket 74. However, the captured stones are unable to leave the capture pocket 74 once lodged therein, owing to the valve-type action of web 76. The snare device 70 of FIG. 7 is adapted for the removal of several stones in the same operation, without the necessity for removing and reinserting the instrument assembly to subsequently capture other stones.

Web 76 is cupped towards the inside of capture pocket 74 and is formed with a plurality of pleats or folds 79 which enable expansion of aperture 78 to accommodate inpassing stones. The pleats 79 resist inversion of web 76 outside of capture pocket 74.

FIG. 8 illustrates a modified snare device or instrument assembly 80 which includes a spring-biased loop 82 provided with a flexible capture pocket 84. A funnel-shaped ancillary web 86 is attached to loop 82 and/or pocket 84 and tapers inwardly into capture pocket 84. An inner end of funnel 86 is provided with a flap 87 which functions as a trap door to hold captured common bile duct stones inside pocket 84. Retained common bile duct stones easily pass through an aperture 88 defined by web 86 and become lodged in capture pocket 84. However, the captured stones are unable to leave the capture pocket 84 once lodged therein, owing to the valve-type action of flap 87.

Although the invention has been described in terms of particular embodiments and applications, one of ordinary skill in the art, in light of this teaching, can generate additional embodiments and modifications without departing from the spirit of or exceeding the scope of the claimed invention. Of course, the trap door feature of FIG. 7 or 8 may be combined with the bent loop 42 of FIG. 5 and/or with the cauterization wire feature of FIG. 6A.

In another embodiment of the invention, a snare as described hereinabove is ejected into the common bile duct from an endoscope which is itself inserted through the biopsy channel of another, larger endoscope. Upon ejection of the smaller "daughter" scope from the biopsy channel of the larger "mother" scope, a distal end of the daughter scope is inserted through the Ampulla of Vater into the common bile duct. The daughter scope is then used to visually inspect the common bile duct for stones. Upon the detection of the stones, a snare device is ejected from the daughter scope into the common bile duct and is used, as discussed above, to remove stones from the duct. In FIG. 2, tubular member 12 may take the form of a daughter scope from which loop 18 is ejected into the common bile duct.

Accordingly, it is to be understood that the drawings and descriptions herein are proffered by way of example to facilitate comprehension of the invention and should not be construed to limit the scope thereof.

What is claimed is:

1. A method for the removal of retained common bile duct stones, comprising the steps of:
   introducing a distal end of a flexible tubular member into the common bile duct;
   ejecting from said distal end a loop to which a flexible web is attached to form a capture pocket;
   upon ejection of said loop from said distal end, expanding said loop and said pocket from a collapsed configuration;
   moving said loop and said pocket through said common bile duct to capture a retained stone in said pocket;
   at least partially closing said loop and said pocket by drawing said loop and said pocket in a proximal direction into said distal end of said tubular member, thereby enclosing the captured stone in said pocket; and
   withdrawing said tubular member and the contracted loop and pocket from the common bile duct, thereby removing the captured stone from the common bile duct,
   said step of introducing including the steps of (i) inserting an endoscope through the stomach and into the upper intestinal tract, (ii) ejecting said tubular member from a biopsy channel in said endoscope, and (iii) inserting said distal end of said tubular member through the Ampulla of Vater into the common bile duct.

2. The method defined in claim 1, further comprising the steps of (a) injecting a radio-opaque fluid into the common bile duct through said tubular member upon insertion of said distal end into the common bile duct, and (b) using an X-ray machine to visually inspect the common bile duct for the locations of stones therein prior to and during said step of moving.

3. The method defined in claim 2 wherein said tubular member is provided with a longitudinally extending elongate window at said distal end and a cauterization wire fastened to said distal end, additionally comprising the steps of (c) exerting tension on said wire upon an ejection of said tubular member from said biopsy channel, thereby bending said tubular member at said distal end to expose a section of said wire through said window, (d) manipulating said tubular member to bring the exposed section of said wire into contact with the Ampulla of Vater, and (e) energizing said wire to cauterize organic tissues during said step of manipulating, thereby enlarging an opening into the common bile duct.

4. The method defined in claim 1, further comprising the steps of (a) ejecting a daughter scope from said biopsy channel, (b) inserting a distal end of said daughter scope through the Ampulla of Vater into the common bile duct, and (c) using said daughter scope to inspect the common bile duct for retained stones, said tubular member being ejected from said daughter scope into the common bile duct.

5. A method for the removal of retained stone from a common bile duct of a patient, comprising the steps of:
providing a flexible tubular member, said tubular member being provided at a distal end with a longitudinally extending elongate window and a cauterization wire fastened to said distal end;
introducing said distal end of said flexible tubular member into the patient;
upon introduction of said distal end of said tubular member into the patient, exerting tension on said wire to bend said tubular member at said distal end to expose a section of said wire through said window;
manipulating said tubular member to bring the exposed section of said wire into contact with an Ampulla of Vater of the patient;
energizing said wire to cauterize organic tissues of the Ampulla of Vater during said step of manipulating, thereby enlarging an opening through the Ampulla of Vater into a common bile duct of the patient;
inserting said distal end of said tubular member through the opening and into the common bile duct;
upon introduction of said distal end of said tubular member into the common bile duct, ejecting from said distal end a capture device;
upon ejection of said capture device from said distal end, expanding said capture device from a collapsed configuration;
moving said capture device through the common bile duct to capture a retained stone in said capture device;
at least partially closing said capture device by drawing said capture device in a proximal direction into said distal end of said tubular member, thereby enclosing the captured stone in said capture device; and
withdrawing said tubular member and the contracted capture device from the common bile duct, thereby removing the captured stone from the common bile duct of the patient.

6. A method for the removal of a retained stone from a common bile duct of a patient, comprising the steps of:
providing a first endoscope with a biopsy channel;
inserting a second endoscope into said biopsy channel;
introducing a distal end of said first endoscope into a patient;
using said first endoscope to visually inspect internal tissues of the patient;
upon visually detecting an opening through an Ampulla of Vater into a common bile duct of the patient, ejecting said second endoscope from said biopsy channel;
upon ejecting of said second endoscope from said biopsy channel, moving said second endoscope in a distal direction and through said opening into the common bile duct;
using said second endoscope to internally inspect the the common bile duct;
upon detecting a retained stone inside the common bile duct with said second endoscope, ejecting, from said second endoscope, a loop to which a flexible web is attached to form a capture pocket;
upon ejection of said loop from said distal end, expanding said loop and said pocket from a collapsed configuration;
moving said loop and said pocket through the common bile duct to capture the retained stone in said pocket;
at least partially closing said loop and said pocket by drawing said loop and said pocket in a proximal direction towards said second endoscope, thereby enclosing the captured stone in said pocket; and
withdrawing said second endocope and the contracted loop and pocket from the common bile duct, thereby removing the captured stone from the common bile duct of the patient.

7. A method for the removal of a retained stone from a common bile duct of a patient, comprising the steps of:
connecting a tubular prosthesis to a common bile duct of the patient so that said tubular prosthesis communicates with the the common bile duct, said tubular prosthesis including a tubular T-bar at an inner end, said step of connecting including the step of disposing said T-bar inside the common bile duct;
introducing a distal end of a flexible tubular member into the common bile duct through said tubular prosthesis and into said common bile duct;
upon introduction of said distal end of said tubular member into the common bile duct, ejecting from said distal end a capture device;
upon ejection of said capture device from said distal end, expanding said capture device from a collapsed configuration;
moving said capture device through common bile duct to capture a retained stone in said capture device;
at least partially closing said capture device by drawing said capture device in a proximal direction into said distal end of said tubular member, thereby enclosing the captured stone in said capture device; and
withdrawing said tubular member and the contracted capture device from the common bile duct through said tubular prosthesis, thereby removing the captured stone from the common bile duct.

8. A method for the removal of retained common bile duct stones, comprising the steps of:
introducing a distal end of a flexible tubular member into the common bile duct;
ejecting from said distal end a loop to which a flexible web is attached to form a capture pocket;
upon ejection of said loop from said distal end, expanding said loop and said pocket from a collapsed configuration;
moving said loop and said pocket through said common bile duct to capture a retained stone in said pocket;

at least partially closing said loop and said pocket by drawing said loop and said pocket in a proximal direction into said distal end of said tubular member, thereby enclosing the captured stone in said pocket; and withdrawing said tubular member and the contracted loop and pocket from the common bile duct, thereby removing the captured stone from the common bile duct, said step of introducing including the steps of (i) connecting a tubular prosthesis to said common bile duct so that said tubular prosthesis communicates with the common bile duct and (ii) inserting said distal end of said tubular member through said tubular prosthesis and into said common bile duct.

9. The method defined in claim 8 wherein said tubular prosthesis includes a tubular T-bar at an inner end, said step of connecting including the step of disposing said T-bar inside the common bile duct.

10. A method for the removal of retained common bile duct stones, comprising the steps of:

introducing a distal end of a flexible tubular member into the common bile duct;

ejecting from said distal end a loop to which a flexible web is attached to form a capture pocket;

upon ejection of said loop from said distal end, expanding said loop and said pocket from a collapsed configuration;

moving said loop and said pocket through said common bile duct to capture a retained stone in said pocket;

at least partially closing said loop and said pocket by drawing said loop and said pocket in a proximal direction into said distal end of said tubular member, thereby enclosing the captured stone in said pocket; and withdrawing said tubular member and the contracted loop and pocket from the common bile duct, thereby removing the captured stone from the common bile duct, said step of expanding including the step of opening said loop to a configuration having a bend so that the expanded loop lies in two planes oriented at an angle with respect to one another.

11. The method defined in claim 10 wherein said step of moving includes the step of pushing the expanded loop in a direction away from said distal end and towards the retained common bile duct stone.

12. A method for the removal of retained common bile duct stones, comprising the steps of:

introducing a distal end of a flexible tubular member into the common bile duct;

ejecting from said distal end a loop to which a flexible web is attached to form a capture pocket;

upon ejection of said loop from said distal end, expanding said loop and said pocket from a collapsed configuration;

moving said loop and said pocket through said common bile duct to capture a retained stone in said pocket;

at least partially closing said loop and said pocket by drawing said loop and said pocket in a proximal direction into said distal end of said tubular member, thereby enclosing the captured stone in said pocket; and withdrawing said tubular member and the contracted loop and pocket from the common bile duct, thereby removing the captured stone from the common bile duct, said pocket being formed with a trap door, further comprising the steps of closing said trap door upon capture of the stone in said pocket and moving said loop to capture another retained common bile duct stone in said pocket.

* * * * *